US009744233B2

(12) United States Patent
Kaplan et al.

(10) Patent No.: US 9,744,233 B2
(45) Date of Patent: Aug. 29, 2017

(54) METHODS OF TREATING AUTOIMMUNE DISEASES

(71) Applicant: GENZYME CORPORATION, Cambridge, MA (US)

(72) Inventors: Johanne Kaplan, Framingham, MA (US); John McPherson, Framingham, MA (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 13/680,667

(22) Filed: Nov. 19, 2012

(65) Prior Publication Data
US 2015/0044164 A1 Feb. 12, 2015
US 2017/0165360 A9 Jun. 15, 2017

Related U.S. Application Data

(63) Continuation of application No. 12/241,345, filed on Sep. 30, 2008, now abandoned, which is a continuation of application No. PCT/US2007/066416, filed on Apr. 11, 2007, now abandoned.

(60) Provisional application No. 60/744,713, filed on Apr. 12, 2006.

(51) Int. Cl.
*A61K 45/00* (2006.01)
*A61K 47/00* (2006.01)
*A61K 39/395* (2006.01)
*A61K 38/18* (2006.01)
*C07K 16/28* (2006.01)
*A61K 45/06* (2006.01)
*C07K 14/495* (2006.01)
*C07K 16/18* (2006.01)
*A61K 39/00* (2006.01)

(52) U.S. Cl.
CPC ...... *A61K 39/3955* (2013.01); *A61K 38/1841* (2013.01); *A61K 39/39541* (2013.01); *A61K 45/06* (2013.01); *C07K 14/495* (2013.01); *C07K 16/18* (2013.01); *C07K 16/28* (2013.01); *C07K 16/2809* (2013.01); *C07K 16/2893* (2013.01); *A61K 2039/505* (2013.01); *C07K 2317/73* (2013.01)

(58) Field of Classification Search
None
See application file for complete search history.

(56) References Cited

U.S. PATENT DOCUMENTS 6,759,035 B2 7/2004 Horwitz et al.
2006/0293391 A1* 12/2006 Birck et al. ................... 514/614

FOREIGN PATENT DOCUMENTS

EP 0325471 7/1989
JP 2002128690 5/2002
WO WO 01/66140 9/2001

OTHER PUBLICATIONS

Lee et al., 1996, Transplantation, vol. 6: pp. 1-3.*
Sanvito et al., 1995, Biochem Biophys Res. Comm. vol. 217: 1279-1286.*
Ellis et al., 2013, Immunology, vol. 139: 179-86.*
Greco et al., 1983, Blood, vol. 62: 1047-54.*
Lauwerys et al., 2000, pp. 1-17.*
Beebe et al., 2002, Cyto. Growth Factor Rev. vol. 13: 403-412.*
Crow, 2010, Rheum Dis Clin North Am. vol. 36: 1-13.*
Tarkowski, el al., Use of Anti-Thymocyte Globulin in the Management of Refractory Systemic Autoimmune Diseases, Rheumatology, vol. 22, No. 6, pp. 261-266, (1993).
Kapanci, et al., Cytoskeletal Protein Modulation in Pulmonary Alveolar Myofibroblasts During Idiopathic Pulmonary Fibrosis, Am J Respir Crit Care Med, vol. 152, pp. 2163-2169, (1994).
Kuwahara, et al., Transforming Growth Factor-B Function Blocking Prevents Myocardial Fibrosis and Diastolic Dysfunction in Pressure-Overloaded Rats, Circulation, (2002), vol. 106, pp. 130-135.
Calabresi, et al., Phase 1 Trial of Transforming Growth Factor Beta 2 in Chronic Progressive MS, Neurology, (1998), vol. 51, pp. 289-292.
Murphy-Ullrich, et al., Activation of Latent TGF-B by Thrombospondin-1: Mechanisms and Physiology, Cytokine & Growth Factor Reviews, vol. 11, (2000), pp. 59-69.
Wing, et al., CD4+CD25-Regulatory T Cells from Mouse to Man, Scand, J. Immunol., vol. 62, No. 1, pp. 1-15, (2005).
Jonuleit, et al., The Regulatory T Cell Farniiy: Distinct Subsets and Their Interrelations, J Immunol, (2003). vol. 171, pp. 6323-6327.
Horwitz, et al., The Role of the Combination of IL-2 and TGF-B or IL-10 in the Generation and Function of CD4+ CD25+ and CD8+, Journal of Leukocyte Biology, vol. 74, (2003), pp. 471-478.
Gorelik, et al., Transforming Growth Factor-B in T-Cell Biology, Nature Reviews Immunology, vol. 2, pp. 46-63, (2002).
Chen, et al., Conversion of Peripheral CD4+CD25-Naive T Cells to CD4+CD25+ Regulatory T Cells by TGF-B Induction of Transcription Factor Foxp3, The Journal of Experimental Medicine, vol. 198, No. 12, (2003), pp. 1875-1886.
Marie, et al., TGF-B1 Maintains Suppressor Function and Foxp3 Expression in CD4+CD25+ Regulatory T Cells, J Exp. Med., vol. 201, No. 7, (2005), pp. 1061-1067.
Huber, et al., Cutting Edge: TGF-B Signaling is Required for the In Vivo Expansion and Immunosuppressive Capacity of Regulatory CD4+CD25+ T Cells1, J. Immunol., vol. 173, pp. 5525-6531, (2004).

(Continued)

*Primary Examiner* — Amy Juedes
(74) *Attorney, Agent, or Firm* — Steptoe & Johnson LLP

(57) ABSTRACT

Novel methods for treating patients with autoimmune diseases are disclosed. The methods of the invention include first depleting circulating lymphocytes in the mammal, e.g., by administering anti-thymocyte antibody, and then, during the course of repopulation, administering to the mammal a therapeutically effective amount of latent TGF-β and/or another agent that promotes expansion of regulatory T cells. In certain aspects, the disclosed process results in improved kidney function and survival rates.

13 Claims, 9 Drawing Sheets

(56) References Cited

OTHER PUBLICATIONS

Barrat, et al., In Vitro Generation of Interleukin 10-Producing Regulatory CD4+ T Cell is Induced by Immunosuppresive Drugs and Inhibited by T Helper Typo 1 (Th1)- and Th2-Inducing Cytokines, J. Exp. Med., vol. 195, No. 5. (2902), pp. 613-616.

Gregori, et al., Regulatory T Cells Induoad by 1a, 25-Dihydroxyvitamin D3 and Mycophenolate Mofetil Treatment Mediate Transplantation Tolerance, J Immunol, (2001), vol. 167, pp. 1945-1053.

Battaglia, et al., Rapamycin Selectively Expands CD4+CD25+FoxP3+ Regulatory T Cells, Blood, (2005), vol. 105, pp. 4743-4748.

Kitani, et al., Treatment of Experimental (Trinitrobenzene Sulfonic Acid) Colitis by Intranasal Administration of Transforming Growth Factor (TGF)-B1 Plasmid:TGF-B1-Mediated Suppression of T Helper Cell Type 1 Response Occurs by Interleukin (IL)-10 Induction and IL-12 Receptor B2 Chain Downregulation, J. Exp. Med., vol. 192, No. 1, pp. 41-52, (2000).

Wang, et al., Dexamethasone Regulation of Lung Epithelial Cell and Fibroblast Interleukin-11 Production, Am J Physiol Liung Cell Mal Physiol, vol. 276, pp. L175-L185, (1999).

Progress in Autoimmune Diseases Research, (2005), pp. 1-126.

Saitoh, et al., Depletion of CD8+ Cells Exacerbates Organ-Specific Autoimmune Diseases induced by CD4+ Cells in Semiallogeneic Hosts With MCH Class II Disparity, The Journal of Immunoiogy, vol. 145, pp. 3268-3275, No. 10, (1990).

Pohlers, et al., TGF-B and Fibrosis in Different Organs—Molecular Pathway Imprints, Biochimica et Biophysica Acta, vol. 1792, (2009), pp. 746-756.

Anolik, New Treatments for SLE: Cell-Depleting and Anti-Cytokine Therapies, Best Practice and Research Clinical Rheumatology, vol. 19, No. 5, pp. 859-878, (2005).

Matsushita, et al., Regulatory B Cells Inhibit EAE initiation in Mice While Other B Cells Promote Disease Progression, The Journal of Clinicai Investigation, vol. 118, No. 10, (2008), pp. 3420-3430.

Zhang, et al., Low Dose Rapamycin Exacerbates Autoimmune Experimental Uveitis, Plos One, (2012), vol. 7, No. 5, pp. 1-11.

Zheng, et al., Activation of Natural Killer T Cells in NZB/W Mice Induces Th-1-Type Immune Responses Exacerbating Lupus, The Journal of Clinical Investigation, (2003), vol. 112, No. 8, pp. 1211-1222.

Bach, Regolatoty T Cells Under Scrutiny: Nature Reviews Immunology, vol. 3, pp. 189-198, (2003).

Flanders, et al., Medical Application of Transforming Growth Factor-B, Flanders et al., Clin. Med, Res., vol. 1, pp. 13-20, (2003).

George, et al., In Vivo Inhibition of Rat Stellate Cell Activation by Soluble Transforming Growth Factor B Type II Receptor: A Potential New Therapy for Hepatic Fibrosis, PNAS. (1999), vol. 96, No. 22, pp. 12719-12724.

Bourdage, et al., Comparative Polyclonal Antithymocyte Globulin and Antilymphoctye/Antilymphoblast Globulin Anti-CD Antigen Analysis by Flow Cytometry, Transplantation, vol. 59, pp. 1194-1200, No. 8, (1995).

Bonnefoy-Berard, et al., Antibodies Against Functional Leukocyte Surface Molecules in Polyclonal Antilymphocyte Antithymocyte Globulins, Transplantation, vol. 51, pp. 669-673, 0991).

Morishita, et al., Antithymocyte Globulin for a Patient With Systemic Lupus Erythematosus Complicated by Severe Pancytopenia, The Journal of International Medical Research, (1997), vol. 25, pp. 219-223.

Racke, et al., Evidence of Endogenous Regulatory Function of Transforming Growht Factor-B1 in Experimental Allergic Encephalomyelitis, International Immunology, vol. 4, No. 5, pp. 615-620, (1992).

Cohen, et al., Treatment of Refractory Autoimmune Diseases With Ablative Immunotherapy, Autoimmunity Reviews, vol. 3, (2004), pp. 21-29.

Li, et al., Transforming Growth Factor-B Regulation of immune Responses, Annual Review of Immunology, vol. 24 (2005), pp. 99-146.

Freireich, et al., Quantitative Compatision of Toxicity of Anticancer Agents in Mouse, Rat, Hamster, Dog, Monkey, and Man, Cancer Chemotherapy Reports, vol. 50, No. 4, (1966), pp. 219-244.

Chen, et al., Gene Therapy in Allergic Encephalomyelitis Using Myelin Basic Protein-Specific T Cells Engineered to Express Latent Transforming Growth Factor-B1, PNAS, vol. 95, pp. 12516-12521, (1999).

Murano, et al., Latent TGF-B1-Transduced CD4+ T Cells Suppress the Progression of Allergic Encephalomyelitis, Journal of Leukocyte Biology, vol. 79, (2006), pp. 140-146.

Kuruvilla, et al., Protective Effect of Transforming Growth Factor B1 on Experimental Autoimmune Diseases in Mice, PNAS, vol. 88. pp. 2918-2921, (1991).

International Search Report for WO2007/121233 dated Oct. 25, 2007.

* cited by examiner

```
huTGFβ1  MPPSGLRLLLPLLLPLWLLVLTPGPPAAGLSTCKTIDMELVKRKRIEAIR    50
huTGFβ2  MHYCVLSAF-LILHLV---TV-----ALSLSTCSTLDMDQFMRKRIEARI    41
huTGFβ3  MKMHLQRAL-VVLALLNFATV-----SLSLSTCTTLDFGHIKKKRVEAIR    44 huTGFβ1  GQILSKLRIASPPSQGEVPPGPLPEAVLALYNSTRD---RVAGESAEP-E    96
huTGFβ2  GQILSKLKITSPE-EDYPEPEEVPPEVISIYNSTRDLLQEKASRRAAACE    90
huTGFβ3  GQILSKLRITSPE-EP-TVMTRVYQVLALYNSTRELLEEMHGEREEGCT    92 huTGFβ1  PE-PEADYYAKEVTRVLM------------------------VETH    125
huTGFβ2  RERSDEEYYAKEVYKIDMPPFFPSETVCPVVTEPSGSVGSLCSRQSQVLC   140
huTGFβ3  QENTESEYYAKEIHKFDM-----------------------IQGL    123 huTGFβ1  NEIYDKFKQSTHSIYMFFNTSELREAVPEPVLLSRAELRLLR-RLKLKV-   165
huTGFβ2  GYLDAIPPTFYRPYFRIVRFDVSAMEKNASNLVKAEFRVFRLQNPKARVP   190
huTGFβ3  AEHNELAVCPKGITSKVFRFNVSSVEKNRTNLFRAEFRVLRVPNPSSKRN   164 huTGFβ1  EQHVELYQKYSNN-----SWRYLSNRLLAPSDSPEWLSFDVTGVVRQWLS   210
huTGFβ2  EQRIELYQILKSKDLTSPTQRYIDSKVVKTRAEGEWLSFDVTDAVHEWLH   240
huTGFβ3  EQRIELFQILRPDE-HIAKQRYIGGKNLPTRGTAEWLSFDVTPTVREWLL   213 huTGFβ1  RGGEIEGFRLSAHCSC----------DSRDNTLQVDINGFTTGR---RG   246
huTGFβ2  HKDRNLGFKISLHCPCCTFVPSNNYIIPNKSEELEARFAGIDGTSTYTSG   290
huTGFβ3  RRESNLGLEISIHCPCHTFQPNGDIL-ENIHEVMEIKFKGVDNEDDHGRG   262
                 + +                                  *  *
huTGFβ1  DLTAI------HGMNRP--FLLLMATPLERAQHLQSSRHRRALDTNYCFS   288
huTGFβ2  DQKTIKSTRKKNSGKTPHLLLMLLPSYRLESQ-QTNRRKKRALDAAYCFR   339
huTGFβ3  DLGRLK---KQKDHHNPHLILMMIPPHRLDNPGQGGQRKKRALDTNYCFR   309
          *
huTGFβ1  STEKNCCVRQLYIDFRKDLGWKWIHEPKGYNANFCSGPCPYIWSLDTQYS   338
huTGFβ2  NVQDNCCLRPLYIDFKRDLGWKWIHEPKGYNANFCAGACPYLWSSDTQHS   389
huTGFβ3  NLEENCCVRPLYIDFRQDLGWKWVHEPKGYYANFCSGPCPYLRSADTTHS   359 huTGFβ1  KVLALYNQHNPGASAAPCCVPQALEPLPIVYYVGRKPKVEQLSNMIVRSC   388
huTGFβ2  RVLSLYNTINPEASASPCCVSQDLEPLTILYYIGKTPKIEQLSNMIVKSC   439
huTGFβ3  TVLGLYNTLNPEASASPCCVPQDLEPLTILYYVGRTPKVEQLSNMVVKSC   409
                       #
huTGFβ1  KCS    391
huTGFβ2  KCS    442
huTGFβ3  KCS    412
```

*FIG. 1*

SEQUENCE LISTING

```
<160> NUMBER OF SEQ ID NOS: 3

<210> SEQ ID NO 1
<211> LENGTH: 391
<212> TYPE: PRT
<213> ORGANISM: Homo sapiens

<400> SEQUENCE: 1

Met Pro Pro Ser Gly Leu Arg Leu Leu Pro Leu Leu Leu Pro Leu Leu
1               5                   10                  15

Trp Leu Leu Val Leu Thr Pro Gly Pro Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Ile Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95
```

```
Pro Glu Pro Glu Ala Asp Tyr Ala Lys Glu Val Thr Arg Val Leu
            100                 105                 110

Met Val Glu Thr His Asn Glu Ile Tyr Asp Lys Phe Lys Gln Ser Thr
            115                 120                 125

His Ser Ile Tyr Met Phe Phe Asn Thr Ser Glu Leu Arg Glu Ala Val
        130                 135                 140

Pro Glu Pro Val Leu Leu Ser Arg Ala Glu Leu Arg Leu Leu Arg Arg
145                 150                 155                 160

Leu Lys Leu Lys Val Glu Gln His Val Glu Leu Tyr Gln Lys Tyr Ser
                165                 170                 175

Asn Asn Ser Trp Arg Tyr Leu Ser Asn Arg Leu Leu Ala Pro Ser Asp
            180                 185                 190

Ser Pro Glu Trp Leu Ser Phe Asp Val Thr Gly Val Val Arg Gln Trp
        195                 200                 205

Leu Ser Arg Gly Gly Glu Ile Glu Gly Phe Arg Ile Ser Ala His Cys
    210                 215                 220

Ser Cys Asp Ser Arg Asp Asn Thr Leu Gln Val Asp Ile Asn Gly Phe
225                 230                 235                 240

Thr Thr Gly Arg Arg Gly Asp Leu Thr Ala Ile His Gly Met Asn Arg
                245                 250                 255

Pro Phe Leu Leu Leu Met Ala Thr Pro Leu Glu Arg Ala Gln His Leu
            260                 265                 270

Gln Ser Ser Arg His Arg Arg Ala Leu Asp Thr Asn Tyr Cys Phe Ser
        275                 280                 285

Ser Thr Glu Lys Asn Cys Cys Val Arg Gln Leu Tyr Ile Asp Phe Arg
    290                 295                 300

Lys Asp Leu Gly Trp Lys Trp Ile His Glu Pro Lys Gly Tyr His Ala
305                 310                 315                 320

Asn Phe Cys Leu Gly Pro Cys Pro Tyr Ile Trp Ser Ile Asp Thr Gln
                325                 330                 335

Tyr Ser Lys Val Leu Ala Leu Tyr Asn Gln His Asn Pro Gly Ala Ser
            340                 345                 350

Ala Ala Pro Cys Cys Val Pro Gln Ala Leu Glu Pro Leu Pro Ile Val
        355                 360                 365

Tyr Tyr Val Gly Arg Lys Pro Lys Val Glu Gln Leu Ser Asn Met Ile
    370                 375                 380

Val Arg Ser Cys Lys Cys Ser
385                 390

<210> SEQ ID NO 2
<211> LENGTH: 442
<212> TYPE: PRT
<213> ORGANISM: Homo sapiens

<400> SEQUENCE: 2

Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
            20                  25                  30

Met Arg Lys Arg Ile Glu Ala Arg Ile Gly Gln Ile Leu Ser Lys Leu
        35                  40                  45

Lys Ile Thr Ser Pro Pro Glu Asp Tyr Pro Glu Pro Glu Glu Val Pro
    50                  55                  60

Pro Glu Val Ile Ser Ile Tyr Asn Ser Thr Arg Asp Leu Leu Gln Glu
```

```
            65                  70                  75                  80
Lys Ala Ser Arg Arg Ala Ala Cys Glu Arg Glu Arg Ser Asp Glu
                    85                  90                  95
Glu Tyr Tyr Ala Lys Glu Val Tyr Lys Ile Asp Met Pro Pro Phe Phe
               100                 105                 110
Pro Ser Glu Thr Val Cys Pro Val Thr Thr Pro Ser Gly Ser Val
               115                 120                 125
Gly Ser Leu Cys Ser Arg Gln Ser Gln Val Leu Cys Gly Tyr Leu Asp
        130                 135                 140
Ala Ile Pro Pro Thr Phe Tyr Arg Pro Tyr Phe Arg Ile Val Arg Phe
145                 150                 155                 160
Asp Val Ser Ala Met Glu Lys Asn Ala Ser Asn Leu Val Lys Ala Glu
                165                 170                 175
Phe Arg Val Phe Arg Leu Gln Asn Pro Lys Ala Arg Val Pro Glu Gln
                180                 185                 190
Arg Ile Glu Leu Tyr Gln Ile Leu Lys Ser Lys Asp Leu Thr Ser Pro
            195                 200                 205
Thr Gln Arg Tyr Ile Asp Ser Lys Val Val Lys Thr Arg Ala Glu Gly
        210                 215                 220
Glu Trp Leu Ser Phe Asp Val Thr Asp Ala Val His Glu Trp Leu His
225                 230                 235                 240
His Lys Asp Arg Asn Leu Gly Phe Lys Ile Ser Leu His Cys Pro Cys
                245                 250                 255
Cys Thr Phe Val Pro Ser Asn Asn Tyr Ile Ile Pro Asn Lys Ser Glu
                260                 265                 270
Glu Leu Glu Ala Arg Phe Ala Gly Ile Asp Gly Thr Ser Thr Tyr Thr
            275                 280                 285
Ser Gly Asp Gln Lys Thr Ile Lys Ser Thr Arg Lys Lys Asn Ser Gly
        290                 295                 300
Lys Thr Pro His Leu Leu Leu Met Leu Leu Pro Ser Tyr Arg Leu Glu
305                 310                 315                 320
Ser Gln Gln Thr Asn Arg Arg Lys Lys Arg Ala Leu Asp Ala Ala Tyr
                325                 330                 335
Cys Phe Arg Asn Val Gln Asp Asn Cys Cys Leu Arg Pro Leu Tyr Ile
                340                 345                 350
Asp Phe Lys Arg Asp Leu Gly Trp Lys Trp Ile His Glu Pro Lys Gly
            355                 360                 365
Tyr Asn Ala Asn Phe Cys Ala Gly Ala Cys Pro Tyr Leu Trp Ser Ser
        370                 375                 380
Asp Thr Gln His Ser Arg Val Leu Ser Leu Tyr Asn Thr Ile Asn Pro
385                 390                 395                 400
Glu Ala Ser Ala Ser Pro Cys Cys Val Ser Gln Asp Leu Glu Pro Leu
                405                 410                 415
Thr Ile Leu Tyr Tyr Ile Gly Lys Thr Pro Lys Ile Glu Gln Leu Ser
            420                 425                 430
Asn Met Ile Val Lys Ser Cys Lys Cys Ser
            435                 440

<210> SEQ ID NO 3
<211> LENGTH: 412
<212> TYPE: PRT
<213> ORGANISM: Homo sapiens

<400> SEQUENCE: 3
```

```
Met Lys Met His Leu Gln Arg Ala Leu Val Leu Ala Leu Leu Asn
1               5                   10                  15

Phe Ala Thr Val Ser Leu Ser Leu Ser Thr Cys Thr Thr Leu Asp Phe
            20                  25                  30

Gly His Ile Lys Lys Lys Arg Val Glu Ala Ile Arg Gly Gln Ile Leu
                35                  40                  45

Ser Lys Leu Arg Ile Thr Ser Pro Pro Glu Pro Thr Val Met Thr His
    50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Gly Cys Thr Gln Glu Asn Thr
                85                  90                  95

Glu Ser Glu Tyr Tyr Ala Lys Glu Ile His Lys Phe Asp Met Ile Gln
            100                 105                 110

Gly Leu Ala Glu His Asn Glu Leu Ala Val Cys Pro Lys Gly Ile Thr
                115                 120                 125

Ser Lys Val Phe Arg Phe Asn Val Ser Ser Val Glu Lys Asn Arg Thr
    130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
                180                 185                 190

Thr Arg Gly Thr Ala Glu Trp Leu Ser Phe Asp Val Thr Asp Thr Val
                195                 200                 205

Arg Glu Trp Leu Leu Arg Arg Glu Ser Asn Leu Gly Leu Glu Ile Ser
    210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
                260                 265                 270

His His Asn Pro His Leu Ile Leu Met Met Ile Pro Pro His Arg Leu
                275                 280                 285

Asp Asn Pro Gly Gln Gly Gln Arg Lys Lys Arg Ala Leu Asp Thr
                290                 295                 300

Asn Tyr Cys Phe Arg Asn Leu Glu Glu Asn Cys Cys Val Arg Pro Leu
305                 310                 315                 320

Tyr Ile Asp Glu Arg Gln Asp Leu Gly Trp Lys Trp Val His Glu Pro
                325                 330                 335

Lys Gly Tyr Tyr Ala Asn Phe Cys Ser Gly Pro Cys Pro Tyr Leu Arg
                340                 345                 350

Ser Ala Asp Thr Thr His Ser Thr Val Leu Gly Leu Tyr Asn Thr Leu
                355                 360                 365

Asn Pro Glu Ala Ser Ala Ser Pro Cys Cys Val Pro Gln Asp Leu Glu
                370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
                405                 410
```

METHODS OF TREATING AUTOIMMUNE DISEASES

This application is Continuation of U.S. application Ser. No. 12/241,345, filed on Sep. 30, 2008, which is a Continuation of International Application No. PCT/US2007/066416, filed on Apr. 11, 2007, which claims the benefit under 35 U.S.C. §119 of U.S. provisional application No. 60/744,713, filed on Apr. 12 2006, all of which are hereby incorporated by reference in their entirety herein.

FIELD OF THE INVENTION

This invention relates to methods of treating autoimmune diseases. The methods of the invention involve the use of latent TGF-β or other agents that stimulate regulatory T cells, alone or in combination with lymphocyte-depleting agents, such as, e.g., anti-thymocyte globulin (ATG).

BACKGROUND OF THE INVENTION

The production of antibodies against self-antigens and/or autoreactive T cells is a hallmark of many autoimmune diseases. Autoantibodies and autoreactive T cells can cause severe tissue damage (e.g., as in lupus nephritis) or loss of blood components (e.g., as in immune thrombocytopenia purpura).

Typically, autoimmune diseases are treated with nonspecific immunosuppressive agents, such as, e.g., cyclophosphamide, methotrexate, azathioprine, and cyclosporine, that impede the immune cells from attacking the organs and tissues. However, immunosuppressive agents are often associated with significant side effects (e.g., toxicity, the undesired suppression of the immune system, etc.).

Due to its immunosuppressive effects, transforming growth factor-beta (TGF-β) has been suggested as a possible therapeutic agent for certain autoimmune diseases, including multiple sclerosis and graft-versus-host disease. Flanders et al., Clin. Med. Res., 1:13-20 (2003). It has also been reported as useful to induce the generation of suppressor T cells in vitro (see, e.g., U.S. Pat. No. 6,759,035). However, TGF-β is a pluripotent cytokine-besides having immunosuppressive properties, it is involved in the extracellular matrix production, and other biological processes. For a review on TGF-β, see, e.g., Cytokine Reference, eds. Oppenheim et al., Academic Press, San Diego, Calif., 2001. Excessive or persistent expression of TGF-β plays a role in organ fibrosis (Kapanci et al., Am. J. Resp. Crit. Care Med., 152:2163-2169 (1995); George et al., Prot. Natl. Acad. Sci., 96:2719-12724 (1999); Kuwahara et al., Circulation, 106: 130-135 (2002)), while systemic administration of active TGF-β has been associated with unacceptable toxicity. In particular, in a Phase I/II clinical trial for chronic progressive multiple sclerosis, systemic administration of active TGF-β2 resulted in unacceptable renal toxicity as evidenced by a reduction in glomerular filtration rate. Calabresi et al., Neurology, 51:289-292 (1998). This result has hindered further clinical development of therapies involving systemic administration of active TGF-β. Accordingly, the challenge of selectively harnessing the immunosuppressive potential of TGF-β without incurring its attendant toxicities has remained. In addition, there remains a need to develop methods of treating autoimmune diseases that allow suppression of autoreactive immunity without undesirable side effects.

SUMMARY OF THE INVENTION

The present invention is based, in part, on the discovery and demonstration that latent TGF-β may be used to circumvent systemic toxicity of active TGF-β. Activation of latent TGF-β requires removal of the latency-associated peptide (LAP) which can occur in vivo through a number of mechanisms including proteolytic cleavage, exposure to reactive oxygen species, and interactions with thrombospondin and other proteins. Murphy-Ullrich et al., Cytokine Growth Factor Rev., 11:59-69 (2000). It is theorized, but not relied on for the purposes of this invention, that such conditions are likely to occur in areas of autoimmune inflammation, such as in the kidney in lupus patients. Because the activation of latent TGF-β occurs in areas of inflammation and tissue injury, the use of latent TGF-β may avoid the toxicity associated with systemic TGF-β. Accordingly, in some embodiments, the methods of the invention involve systemic administration of inactive TGF-β (e.g., latent TGF-β) to a mammal, whereupon the activation and/or action of TGF-β is limited to sites of inflammation and tissue damage.

The present invention is further based, in part, on the discovery and demonstration that depletion of lymphocytes by anti-thymocyte globulin (ATG) followed by administration of latent TGF-β is effective in improving kidney function and increasing survival rates in a murine model of systemic lupus erythematosus. Accordingly, in some embodiments of the invention, host lymphocytes are depleted prior to the administration of latent TGF-β so as to yield the therapeutically desired effect of the latent TGF-β administration.

It is further theorized, but not relied on for the purposes of this invention, that the therapeutic effect of TGF-β is achieved, in part, due to the stimulatory effects of TGF-β on the growth of regulatory T cells. Therefore, in some embodiments of the invention, another agent that promotes the expansion of regulatory T cells may be administered in place of, or in addition to, latent TGF-β.

This invention provides methods for treating a mammal (e.g., a human) with an autoimmune disease, e.g., systemic lupus erythematosus (SLE), rheumatoid arthritis (RA). In some embodiments, the treatment results in slowing the progression of disease and/or improvement in symptoms. The invention further provides methods of preserving or improving kidney function in a mammal with an autoimmune disease that impairs kidney function, such as, e.g., SLE, Goodpasture's syndrome, Wegener's syndrome, and Berger's disease.

In more particular embodiments, the methods of the invention include the following steps:
(a) depleting circulating lymphocytes in a mammal,
(b) allowing the lymphocytes to begin repopulating ("repopulation phase"), and
(c) during the repopulation phase, administering to the mammal a therapeutically effective amount of latent TGF-β and/or an agent that promotes the expansion of regulatory T cells.

In some embodiments, the depletion of lymphocytes is accomplished by administering anti-thymocyte antibody (e.g., Thymoglobulin®, Atgam™, Fresenius™, and Tecelac™) or another antibody specific for an antigen(s) expressed on T cells.

Once the circulating lymphocytes have been substantially depleted, they are allowed to start repopulating ("repopulation phase"). During the course of repopulation, before the complete repopulation occurs, a therapeutically effective amount of one or more of the following agents is administered to the mammal: (1) latent TGF-β (e.g., the latent form of any one of TGFβ1-TGFβ3) and/or (2) one or more other agents that promotes expansion of regulatory T cells (e.g., IL-10, IL-10 and IL-4, IL-10 and IFN-α, vitamin D3 and dexamethasone, vitamin D3 and mycophenolate mofetil, and rapamycin).

In some embodiments, where the kidney function is compromised due to autoimmune disease, the treatment methods result in improvement of kidney function in the mammal (e.g., slowing the loss thereof) as indicated by, e.g., a change in systemic blood pressure, proteinuria, albuminuria, glomerular filtration rate, and/or renal blood flow.

The foregoing summary and the following detailed description are exemplary and explanatory only and are not restrictive of the invention, as claimed.

BRIEF DESCRIPTION OF THE FIGURES

FIG. 1 shows an alignment of amino acid sequences of the precursors of human TGF-β1 (SEQ ID NO:1), TGF-β2 (SEQ ID NO:2), and TGF-β3 (SEQ ID NO:3). TGF-β2 is shown in the 'long' alternatively spliced form in which a 28 amino acid insertion is found in the pre-pro domain beginning at residue 119. Conserved sequences are boxed in. Arrows indicate the sites of proteolytic processing resulting in cleavage of the signal peptide and of the mature C-terminal TGF-β1 fragment. * refers to RGD integrin recognition site found in the latency-associated peptide (LAP) proteins of TGF-β1 and TGF-β3. + refers to cysteine residues involved in disulfide bonds between the two monomeric LAP proteins. # refers to a cysteine residue involved in formation of the single disulfide bond TGF-β monomers.

DETAILED DESCRIPTION OF THE INVENTION

Figure 2:
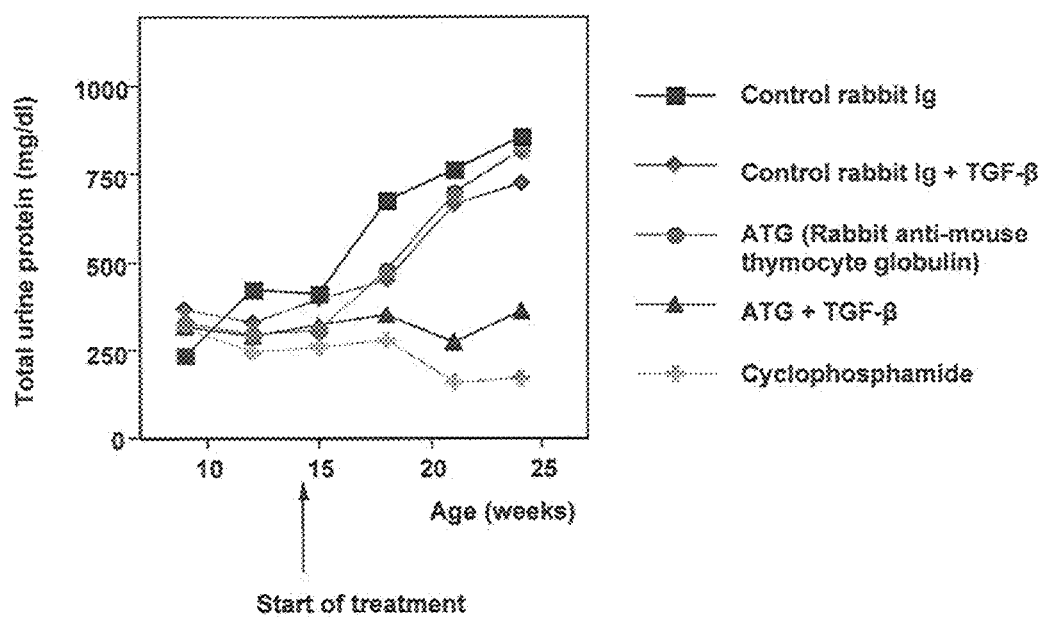
FIG. 2 shows the therapeutic effect of the ATG/latent TGF-β1 combination treatment on kidney function. MRL/MPJ-Tnfrs6$^{lpr}$ mice (a murine model of SLE) were injected with 500 μg of ATG intraperitoneally (i.p.) twice, three days apart, with or without 4 μg of latent TGF-β1 in 100 μl of phosphate buffered saline (PBS). Four micrograms of latent TGF-β1 corresponds to a 1 μg (~0.05 mg/kg) dose of the active (mature, non-LAP-associated) portion of the molecule. When included in a treatment, the latent TGF-β1 was administered daily for twelve days beginning eleven days after the second ATG injection. As a negative control, SLE mice were treated with 500 μg of normal rabbit immunoglobulin (Ig) i.p. twice, three days apart. An additional treatment group received normal rabbit immunoglobulin and latent TGF-β1 administered as above. As a positive control, SLE mice were treated with 100 mg/kg i.p. of cyclophosphamide in 200 μl saline weekly. Proteinuria was significantly lower in SLE mice treated with latent TGF-β1 and ATG as compared to SLE mice treated with either ATG alone, control Ig+TGF-β1, or control Ig alone. Mean total urine protein of the combination treatment group approached the level achieved with cyclophosphamide, a current treatment for lupus.

This invention provides methods of treating a mammal with an autoimmune disease. In particular embodiments, such methods include methods of improving kidney function in a mammal with an autoimmune disease that compromises kidney function. In some embodiments, the methods of the invention involve systemic administration of latent TGF-β to a mammal, wherein the activation and/or action of TGF-β is limited to sites of inflammation and tissue damage.

In some embodiments, methods of the invention comprise the following steps:
(a) depleting circulating lymphocytes in the mammal,
(b) allowing the lymphocytes to begin repopulating, and
(c) during the repopulation phase of (b), administering to the mammal a therapeutically effective amount of latent TGF-β and/or an agent that promotes the expansion of regulatory T cells.

Lymphocyte Depletion

Depletion of circulating lymphocytes can be accomplished by administering a lymphocyte-depleting agent to the mammal or otherwise exposing the mammal to conditions that result in a loss of a substantial fraction of lymphoid cells (e.g., lymphocytes, natural killer (NK) cells, monocytes, and/or dendritic cells, etc.) in the mammal. Lymphocytes to be depleted may be T lymphocytes (T cells) and/or T and B lymphocytes. In the depletion phase, T cell counts are reduced by at least 30%, 40%, 50%, 60%, 70%, 80%, 90%, 95%, or more, and optionally, B lymphocyte (B cell) counts are reduced by at least 30%, 40, 50%, 60%, 70%, 80%, 90%, 95%, or more. In preferred embodiments, the depleted lymphocytes are predominantly T cells, which means that the percentage of depleted T cells is greater (e.g., 1.2-, 1.5-, 2-, 5-, 10-fold, or more) than the percentage of depleted B cells.

The level of lymphocyte depletion can be readily assessed by, for example, measuring the amount of peripheral blood lymphocytes (PBLs). Lymphocyte counts can be determined using conventional clinical laboratory techniques (e.g., by flow cytometry). Reference values for normal PBL levels in humans are presented in Table 1.

TABLE 1

| Cell Type | Typical Marker | Mean (%) | Range (%) | Mean (cells/μl) | Range (cells/μl) |
|---|---|---|---|---|---|
| Total T cells | CD3 | 71 | 55-87 | 1,586 | 781-2,391 |
| Total B cells | CD19 | 5 | 1-9 | 277 | 17-537 |
| Helper T cells | CD4 | 43 | 24-62 | 1,098 | 447-1,750 |
| Cytotoxic cells | CD8 | 42 | 19-65 | 836 | 413-1,260 |

In some embodiments, the lymphocyte-depleting agent is an anti-lymphocyte antibody, e.g., anti-T cell antibodies, e.g., anti-thymocyte globulin (ATG), such as, e.g., Thymoglobulin®, Atgam™, Fresenius™, and Tecelac™. ATG is a polyclonal antibody directed against thymocytes. Currently marketed ATG products are produced by injecting thymocytes from one species (e.g., human) into another species (e.g., rabbit or horse). ATG binds to cell surface proteins such as lymphocyte surface antigens CD2, CD3, CD4, CD8, CD11a, CD18, CD25, HLA DR, and HLA class I (Bourdage et al., Transplantation, 59:1194-1200 (1995)). ATG is believed to induce immunosuppression primarily as a result of T cell depletion (see, e.g., Bonnefoy-Bérnard et al., Transplantation, 51:669-673 (1991)) and has been previously used for pretreating transplant patients to reduce the risk of rejection in the context of organ transplantation.

In addition to ATG, the lymphocyte-depleting agent consists of or comprises a monoclonal or polyclonal antibody directed to one or more specific lymphocyte surface antigens, e.g., anti-CD52 antibody (e.g., Campath®), anti-CD3 antibody (e.g., OKT3®), anti-CD4 antibody (OKT™), anti-CD25 (IL-2R) antibody (e.g., daclizumab), anti-CD5 antibody, anti-CD7 antibody, anti-TCR antibody, anti-CD2 (e.g., Siplizumab™), or an antibody against any of other lymphocyte surface antigens specified above, etc.

In some embodiments, the lymphocyte-depleting agent is a corticosteroid.

In some embodiments, conditions that result in depletion of lymphocytes include exposure to gamma radiation.

A combination of any suitable agents and/or conditions to deplete lymphocytes can be also used.

Reconstitution Phase

Following the depletion phase, the lymphocytes of the mammal are allowed to begin repopulating by withdrawing the lymphocyte-depleting agent or mitigating the conditions that resulted in the loss of lymphocytes.

While in some instances, the agent of step (c) (i.e., TGF-β or another agent that specifically stimulates regulatory T cells) can be administered to the mammal immediately at the start of the replenishment phase, in other cases, the agent is administered after some repopulation has occurred. Before the step (c) agent is administered to the mammal, the lymphocytes may be allowed to repopulate to less than 50%, 40%, 30%, 20%, 10%, 5%, or lower, as compared to the pre-depletion level.

In humans, lymphocytes repopulate to pre-depletion levels at different rates depending on the depleting agent. For example, with ATG, a complete repopulation may take two to four months, while after treatment with Campath™, the repopulation may take several years. Accordingly, in some embodiments, the length of time between the end of the depletion phase of the lymphocytes and the administration of step (c) agent is, for example, 0, 1, 2, 3, 4, 5, 6 days; 1, 2, 3, 4, or 5 weeks, or longer.

TGF-β

In certain embodiments, the methods of the invention involve administration of inactive TGF-β which is activated after administration. In some embodiments, inactive TGF-β is administered in the form of latent TGF-β. In other embodiments, inactive TGF-β is administered in the form of a TGF-β-encoding DNA which expresses active TGF-β upon induction.

TGF-β is naturally secreted in either a so-called "small latent complex" (100 kDa) in which the biologically active TGF-β is noncovalently associated with its pro domain ("latency-associated peptide," LAP) and in a so-called "large latent complex" (220 kDa) additionally containing latent TGF-β biding protein (LTBP). The latent forms are unable to bind to TGF-β receptors until active, i.e., mature, TGF-β is released from the complex. For a more detailed review of the latent forms and activation process, see, e.g., Cytokine Reference, eds. Oppenheim et al., Academic Press, San Diego, Calif., 2001, pp. 724-725. As used herein, the term "latent TGF-β" refers to TGF-β associated with LAP (covalently or noncovalently) and, optionally, additionally associated with LTBP (covalently or noncovalently). The term, therefore, refers to small and large latent TGF-β complexes. Other forms of inactive TGF-β that could be activated in the locations and at the time periods desired would also be useful in the methods of this invention. There are three known mammalian isoforms of TGF-β (TGF-β1 to TGF-β3), all of which are homologous among each other (60-80% identity). A partial listing of protein accession number for the three mammalian isoforms is provided in Table 2; an alignment of human TGF-βs is shown in FIG. 1.

TABLE 2

| Species | TGF-β1 | TGF-β2 | TGF-β3 |
| --- | --- | --- | --- |
| Human | P01137 | P08112 | P109600 |
| Mouse | P04202 | P27090 | P171125 |
| Rat | AAD20222 | AAD24484 | Q07258 |
| Porcine | AAA616 | AAB03850 | P15203 |
| Simian | P09533 | WFMKB2 | |

The structural and functional aspects of TGF-β as well as TGF-β receptors are well known. See, e.g., Cytokine Reference, eds. Oppenheim et al., Academic Press, San Diego, Calif., 2001. Thus, inactivated forms of engineered TGF-βs that retain the ability to bind to one or more TGF-β receptors (TGF-βRI, TGF-βRII, or TGF-βRIII) would also be useful in the methods of the invention. Such inactivated forms of engineered TGF-β may contain only a partial or a mutated amino acid sequence of the naturally occurring TGF-β. For example, inactivated forms of engineered TGF-β may contain native sequences in which conservative substitutions were made and/or nonessential amino acids were deleted. For example, they may comprise a sequence, which is at least 80%, 85%, 90%, 95%, 96%, 97%, 98%, 99%, or 100% identical to the 112 amino acid C-terminal portion of SEQ ID NO:n over the entire length of this C-terminal portion of SEQ ID NO:n, wherein n=1, 2, or 3.

Agents that Promote Regulatory T Cell Expansion

In certain embodiments, the methods of the invention involve administration of an agent that promotes regulatory T cells expansion. Regulatory T cells (also known as Tregs or suppressor T cells) are cells that are capable of inhibiting the proliferation and/or function of other lymphoid cells via contact-dependent or contact-independent (e.g. cytokine production) mechanisms. Several types of regulatory T cells have been described, including γδ T cells, Natural Killer T (NKT) cells, CD8$^+$ T cells, CD4$^+$ T cells, and double negative CD4$^-$ CD8$^-$ T cells. See, e.g., Bach et al., Immunol., 3:189-98 (2003). The so-called "naturally occurring" regulatory T cells are CD4$^+$ CD25$^+$ and express the forkhead family transcription factor FOXP3 (forkhead box p3). In addition to the FOXP3-expressing CD4$^+$ CD25$^+$, a minor population of CD8$^+$ FOXP3-expressing cells are also regulatory T cells. CD4$^+$ Tregs can be further divided into induced regulatory T cells that secrete interleukin-10 (IL-10) and TGF-β such as Tr1 cells and T-helper 3 (Th3) cells. Additional surface markers for CD4$^+$ CD25$^+$ regulatory T cells include CD45RB, CD38, GITR, surface TGF-β, CTLA4, CD103, CD134 and CD62L. For a detailed review of various types of regulatory T cells, see, e.g., Wing et al., Scand. J. Immunol., 62(1):1 (2005); Jonuleit et al., J. Immunol., 171:6323-6327 (2003); Horwitz et al., J. Leukocyte Biol., 74:471-478 (2003).

Accordingly, in some embodiments, the regulatory T cells that are being stimulated include one or more of the following groups: (1) regulatory T cells that express IL-10; (2) regulatory T cells that express TGF-β (including Tr1 cells and Th3 cells); (3) CD4$^+$ CD25$^+$ cells (including cells having additional markers CD45RB$^+$, CD38$^+$, GITR, surface TGF-β, CTLA-4, CD103, CD134 and/or CD62L); (4) FOXP3-expressing T cells (including CD8$^+$ cells and CD4$^+$ cells); (5) γδ T cells; (6) NK T cells; and (7) double negative CD4$^-$ CD8$^-$ T cells.

TGF-β, in addition to its direct immunosuppressive activity, may also be capable of stimulating regulatory T cells. Gorelik and Flavell, Nature Reviews Immunology, 2:46-53 (2002); Chen et al., J. Exp. Med., 198:1875-1886 (2003); Marie et al., J. Exp. Med., 7:1061-1067 (2005); Huber et al., J. Immunol., 173:6526-6531 (2004).

Examples of agents, other than TGF-β, that promote regulatory T cell expansion include: (1) IL-10; (2) IL-10 and IL-4; (3) IL-10 and IFN-α; (4) vitamin D3 and dexamethasone; (5) vitamin D3 and mycophenolate mofetil, and (6) rapamycin. (See, e.g., Barrat et al., J. Exp. Med., 195:603-616 (2002); Jonuleit et al., J. Immunol., 171:6323-6327 (2003); Gregori et al., J Immunol., 167:1945-1953 (2001); Battaglia et al., Blood, 105:4743-4748 (2005).)

In some embodiments, an increase of, e.g., at least 10%, 20%, 30%, 40%, 50%, 100%, or more in the expansion of regulatory T cells in the presence of an agent as opposed to its absence is considered indicative of the agent's capacity to promote regulatory T cells expansion. TGF-β and other agents can be assayed for their capacity to promote regulatory T cell expansion using routine methods. Examples of some of the more frequently used in vitro assays include the following:

(1) flow cytometry analysis, wherein co-expression of CD4, CD25, and/or FOXP3, and/or CD62L, and/or GITR, and/or CTLA4, and/or surface TGF-β, and/or CD103, and/or CD134 is used as indication of a regulatory T cell phenotype (see, e.g., Jonuleit, supra);

(2) inhibition of T cell proliferation in a co-culture system as described in, e.g., Chen et al., J. Exp. Med., 198:1875-1886 (2003). (In this assay, regulatory T cells are added to responder T cells and the co-culture is stimulated with anti-CD3 or allogeneic lymphocytes. In the presence of regulatory T cells, the responder T cells become unable to proliferate in response to these stimuli. The degree of proliferation is typically measured by tritiated thymidine incorporation.); and (3) cytokine profiling as described in, e.g., Barrat, supra, and Jonuleit, supra. (In this assay, a supernatant from cultured regulatory T cells is analyzed for the presence of the immunosuppressive cytokines such as, e.g., IL-10 and TGF-β, known to be produced by regulatory T cells.)

Uses

The methods of the invention can be used to treat a mammal that has an autoimmune disease such as, e.g., systemic lupus erythematosus (SLE) and autoimmune rheumatoid arthritis (RA). Examples of mammals include humans or other primates (e.g., chimpanzees), rodents (e.g., mice, rats, or guinea pigs), rabbits, cats, dogs, horses, cows, and pigs. In some of the subjects afflicted, the treatment is expected to result in inhibiting the progression of disease and/or improvement in symptoms.

Examples of additional autoimmune diseases include insulin-dependent diabetes mellitus (IDDM; type I diabetes), inflammatory bowel disease (IBD), graft-versus-host disease (GVHD), celiac disease, autoimmune thyroid disease, Sjögren's syndrome, autoimmune gastritis, autoimmune hepatitis, cutaneous autoimmune diseases, autoimmune dilated cardiomyopathy, multiple sclerosis (MS), myasthenia gravis (MG), vasculitis (e.g., Takayasu's arteritis and Wegener's granulomatosis), autoimmune diseases of the muscle, autoimmune diseases of the testis, autoimmune ovarian disease, autoimmune uveitis, Graves' disease, psoriasis, ankylosing spondylitis, Addison disease, Hashimoto thyroiditis, idiopathic thrombocytopenic purpura, and vitiligo.

The methods of the invention are expected to slow the progression of autoimmune disease, improve at least some symptoms, and/or increase survival. For example, the methods of the invention may result in a reduction in the levels of autoantibodies, B cells producing autoantibodies, and/or autoreactive T cells. The reduction in any of these parameters can be, for example, at least 10%, 20%, 30%, 50%, 70% or more as compared to pretreatment levels.

The invention further provides methods of preserving or improving 6kidney function in a mammal with an autoimmune disease that compromises kidney function. Examples of autoimmune diseases that may compromise kidney function include SLE (e.g., lupus nephritis), Goodpasture's syndrome, Wegener's granulomatosis (Wegener's syndrome), Berger's disease (IgA nephropathy), and IgM nephropathy. In some of the patients afflicted with such diseases, the treatment is expected to result in improvement of kidney function (e.g., slowing the loss of, preserving, or improving the same) as indicated by, e.g., a change in systemic blood pressure, proteinuria, albuminuria, glomerular filtration rate, and/or renal blood flow.

The term "renal function" refers to the ability of a kidney to perform its physiological functions such as pressure filtration, selective reabsorption, tubular secretion, and/or systemic blood pressure regulation. Methods for assessing renal function are well known in the art and include, but are not limited to, measurements of blood systemic and glomerular capillary pressure, proteinuria, albuminuria, microscopic and macroscopic hematuria, serum creatinine level (e.g., one formula for estimating renal function in humans equates a creatinine level of 2.0 mg/dl to 50% of normal kidney function and 4.0 mg/dl to 25%), decline in the glomerular filtration rate (GFR) (e.g., as indicated by the rate of creatinine clearance, or using inulin assays), and degree of tubular damage.

For a detailed review of renal function and related disease states, see The Kidney: Physiology and Pathophysiology, eds. Seldin et al., 3$^{rd}$ ed., Lippincott, Williams & Wilkins Publishers, 2000. Normally, less than 0.15 g of protein is excreted into the urine in a 24-hour period. Almost all types of kidney disease cause mild (up to 500 mg per day) to moderate (up to 4 g per day) protein leakage into the urine. The normal concentration of albumin in the urine is less than 1.0 mg/dl. Generally, 30-300 mg/dl urinary albumin is considered microalbuminuria, and greater than 300 mg/dl is considered macroalbuminuria. The normal values of serum creatinine are 0.6-1.5 mg/dl for men and 0.6-1.1 mg/dl for women. The relationship between creatinine levels, renal function, and the stage of renal disease is shown in Table 3.

TABLE 3

| Creatinine Level (mg/dl) | Estimated Reduction of Renal Function | Stage of Renal Disease |
| --- | --- | --- |
| 0.6-1.5 | Up to 25% | Reduced or diminished renal reserve |
| >1.5 | >50% | Renal insufficiency |
| 4.8 | 75% | Renal failure |
| 10 | 90% | End-stage renal disease |

Therefore, the methods of the invention may be useful in patients having an autoimmune disease with reduced or diminished renal reserve, renal insufficiency, renal failure, or end-stage renal disease. For example, methods of the invention may be used in patient with microalbuminuria, macroalbuminuria, and/or proteinuria levels over 1, 2, 3, 4, 5, 6, 7, 8, 9, or 10 g or more per a 24-hour period, and/or serum creatinine levels of about 1.0, 1.5, 2.0, 2.5, 3.0, 3.5, 4.0, 4.5, 5.0, 5.5, 6.0, 7.0, 8.0, 9.0, 10 mg/dl or higher.

In some embodiments, the methods of the invention reduce the amount of protein secreted in the urine (proteinuria), amount of albumin secreted in the urine (albuminuria), and/or the patient's serum creatinine levels by at least 10%, 20%, 30%, 40%, 50%, 60%, 70%, or more, relative to control subjects. In other embodiments, the methods of the invention slow the loss of renal function by at least 10%, 20%, 30%, 40%, 50%, 60%, 70%, or more, relative to control subjects. Nonlimiting illustrative methods for assessing renal function are described herein and, for example, in WO 01/66140.

Methods of Administration

In the methods of the invention, "administration" is not limited to any particular delivery system and may include, without limitation, parenteral (including subcutaneous, intravenous, intramedullary, intraarticular, intramuscular, or intraperitoneal injection), rectal, topical, transdermal, or oral (for example, in capsules, suspensions, or tablets). Administration to an individual may occur in a single dose or in repeat administrations, and in any of a variety of physiologically acceptable salt forms, and/or with an acceptable pharmaceutical carrier and/or additive as part of a pharmaceutical composition. Physiologically acceptable salt forms and standard pharmaceutical formulation techniques and excipients are well known to persons skilled in the art (see, e.g., Physicians' Desk Reference (PDR®) 2005, 59$^{th}$ ed., Medical Economics Company, 2004; and Remington: The Science and Practice of Pharmacy, eds. Gennado et al. 21th ed., Lippincott, Williams & Wilkins, 2005).

Latent TGF-β can also be administered by means of gene therapy (i.e., by administering a TGF-β-encoding DNA in an appropriate vector), for example, as described in Kitani et al., J. Exp. Med., 192(1):41-52 (2000).

The appropriate effective doses for the latent TGF-β, agents promoting Tregs, and lymphocyte depleting agents will be chosen by a treating clinician and will range roughly from 0.01 μg/kg to 25 mg/kg, from 0.1 μg/kg to 10 mg/kg, from 1 μg/kg to 1 mg/kg, 10 μg/kg to 1 mg/kg, from 10 μg/kg to 100 μg/kg, from 100 μg/kg to 1 mg/kg, and from 500 μg/kg to 5 mg/kg. Additionally, specific dosages indicated in the Examples or in the PDR® 2005 and later editions may be used to arrive at the desired dosage. For example, the currently approved uses of Thymoglobulin® in the United States include transplantation (from 1 mg/kg to 2.5 mg/kg for 2-14 days) and aplastic anemia (from 2.5 mg/kg to 3.5 mg/kg for 5 days).

Effective dosages achieved in one animal may be converted for use in another animal, including humans, using conversion factors known in the art. See, e.g., Freireich et al., Cancer Chemother. Reports, 50(4):219-244 (1966) and Table 4 for equivalent surface area dosage factors. Examples of autoimmune disease models and appropriate methods can be found in, e.g., Cohen et al. (eds.) Autoimmune Disease Models, Academic Press, 2005.

TABLE 4

| | From: | | | | |
| --- | --- | --- | --- | --- | --- |
| To: | Mouse (20 g) | Rat (150 g) | Monkey (3.5 kg) | Dog (8 kg) | Human (60 kg) |
| Mouse | 1 | 0.5 | 0.25 | 0.17 | 0.08 |
| Rat | 2 | 1 | 0.5 | 0.25 | 0.14 |
| Monkey | 4 | 2 | 1 | 0.6 | 0.33 |
| Dog | 6 | 4 | 1.7 | 1 | 0.5 |
| Human | 12 | 7 | 3 | 2 | 1 |

The following Examples are provided for illustrative purposes and are not intended to be limiting.

EXAMPLES

Potency Assessment of Activated TGF-β1

Recombinant human latent TGF-β1 was produced in CHO cells (Genzyme, Framingham, Mass.). Disruption of LAP from latent TGF-β1 was achieved through acidification. LAP-TGF-β1 was diluted to 200 ng/mL in assay medium (DMEM plus non-essential amino acids, L-glutamine, pen-strep, and 10% FBS). Five hundred microliters of the diluted sample was activated by adding 100 μL of 1N HCl and incubating at room temperature for 20 minutes. The sample was subsequently neutralized with 100 μL of 1.2 N NaOH/0.5 M HEPES.

The activated TGF-β1 sample was analyzed using the A549 Cell Potency Assay and the activity assessed in comparison to a human recombinant TGF-β2 (Genzyme, Framingham, Mass.) control. The A549 potency assay is based on the TGF-β1-induced release of IL-11 by the human lung epithelial cell line, A549 and is described in Wang et al., Am. J. Physiol., 276:L175-L185 (1999). IL-11 release from the A549 cells in response to TGF-β1 was measured using an ELISA procedure (R&D Systems, Minneapolis, Minn.).

Murine Lupus Model

Animals and Reagents—

Female MRL/lpr mice were obtained from the Jackson Laboratory (Bar Harbor, Me.) and were received at 5-6 weeks of age. ATG was generated by the immunization of rabbits with Balb/c mouse thymocytes as follows. Rabbits were immunized subcutaneoulsy with $5 \times 10^7$ fresh thymocytes on day 0 and boosted intravenously with $5 \times 10^7$ fresh thymocytes on day 14. Serum collected on days 20, 22, and 25 was pooled and the IgG fraction was isolated by chromatography and sodium sulfate precipitation. A commercial preparation of IgG from naïve rabbits was used as a negative control (Sigma, St. Louis, Mo.). Recombinant human latent TGF-β1 was produced in CHO cells (Genzyme, Framingham, Mass.). Cyclophosphamide was purchased from VWR Scientific Products (West Chester, Pa.).

Treatment—

Animals were monitored for proteinuria, albuminuria, and titers of IgG antibodies to double-stranded DNA (dsDNA) every three weeks (see below). Therapeutic treatment was initiated when animals started developing antibodies to dsDNA and/or elevated proteinuria at 12-13 weeks of age. Treatment with ATG or control rabbit IgG consisted of two intraperitoneal (i.p.) injections of 500 μg (~25 mg/kg) delivered three days apart (days 0 and 3). Latent TGF-β1 was given from days 14-25 as twelve daily i.p. injections of 4 μg per mouse. A 4 μg dose of latent TGF-β1 corresponds to a 1 μg (~0.05 mg/kg) dose of the active (mature, non-LAP-associated) portion of the molecule. Cyclophosphamide was used as a positive control and was delivered i.p. weekly at a dose of 100 mg/kg from 12-13 weeks of age until the end of the study at 24-25 weeks of age. The treatment groups consisted of control rabbit IgG, control rabbit IgG+latent TGF-β1, ATG, ATG+latent TGF-β1, or cyclophosphamide with ten animals per group.

Proteinuria and Albuminuria—

Levels of protein in the urine of individual mice were measured using a colorimetric assay designed to measure total protein concentration. Levels of albumin in the urine were assessed with a quantitative ELISA assay.

A 24-hour urine collection was performed every three weeks by placing mice into individual metabolic cages. Proteinuria was measured using the Microprotein-PR™ kit from Sigma (St. Louis, Mo.) according to manufacturer's instructions. Briefly, urine was added to a reagent solution containing pyrogallol red-molybdate complex. The mixture was incubated at 37° C. for ten minutes to allow for binding of the reagent to basic amino groups on proteins leading to a shift in absorbance at 600 nM. The increase in optical density (O.D.) at 600 nM is directly proportional to protein concentration and a reference standard was used to calculate the protein concentration of test samples according to the following formula:

$$\frac{OD_{sample}}{OD_{standard}} \times Conc_{standard} \times \text{Dilution} = Conc_{sample} (mg/dl)$$

Levels of albumin in the urine were assessed using an indirect competitive ELISA kit, according to manufacturer's instructions (Albuwell M from Exocell Inc, Philadelphia, Pa.). Briefly, serial two-fold dilutions of urine samples were added to duplicate wells of an ELISA plate coated with mouse albumin. Rabbit anti-mouse albumin antibody was then added to the wells allowing for competition between binding of the antibody to albumin in the sample and albumin attached to the well. This was followed by the addition of horseradish peroxidase (HRP)-conjugated anti-rabbit immunoglobulin and HRP substrate to detect the amount of rabbit anti-mouse albumin antibody bound to the well. The O.D. at 450 nm was inversely proportional to the logarithm of the amount of albumin in the urine sample. The albumin concentration in the urine samples was derived from a standard curve obtained with known concentrations of murine albumin.

Anti-dsDNA ELISA—

Titers of IgG antibodies to dsDNA in serum samples from individual mice were measured by ELISA.

Serum samples from individual mice were collected every three weeks. Titers of antibodies to dsDNA were assessed by ELISA. Mouse double-stranded DNA (The Jackson Laboratory) was digested with S1 nuclease (Invitrogen, Carlsbad, Calif.) to remove any single-stranded DNA and was then used to coat the wells of a 96-well ELISA plate (100 μl/well of 1 μg/ml dsDNA) overnight at 4° C. The plates were pretreated with 0.01% protamine sulfate in water (150 μl/well for 90 minutes at room temperature) to facilitate adhesion of the DNA. After coating, the plates were incubated with 2.5% BSA blocking buffer for one hour at 37° C. and washed. One hundred microliters of serial two-fold dilutions of serum were then added to duplicate wells and incubated at 37° C. for one hour. The plates were washed and HRP-conjugated goat anti-mouse IgG (Pierce, Rockford, Ill.) was added to detect antibodies bound to dsDNA (37° C. for one hour). After washing, HRP substrate was added for 30 minutes at room temperature and the O.D. of the colorimetric product was read at 490 nM with a reference wavelength of 650 nM on a dual wavelength plate reader (Molecular Devices, Sunnyvale, Calif.). The antibody titer was defined as the reciprocal of the dilution of serum giving an O.D. greater or equal to 0.1. Normal mouse serum was used as a negative control (titer <200, the lowest dilution tested) and serum from aged MRL/lpr lupus mice was used as a positive control (titer of 6400-25600).

Histology—

Kidneys were collected for histological analysis at the time of scheduled sacrifice or during the course of the study from moribund animals that required euthanasia. The kidneys were sliced longitudinally and were fixed in neutral buffered formalin. Sections of approximately 5 μm were stained with hematoxylin and eosin (H&E) and periodic acid-Schiff (PAS) stains. The slides were scored by pathologist for glomerular morphology, interstitial inflammation, and protein casts according to the scoring systems described in Tables 5A and 5B.

TABLE 5A

Glomeruli

0   No significant lesions (comparable to WHO class I)
1   Minimal to mild disease, characterized by mesangial deposits (comparable to WHO class IIA)
2   Mild to moderate disease, characterized by hypercellularity with or without mesangial deposits (comparable to WHO class IIB)
3   Moderate to severe disease, characterized by mesangioproliferative glomerulopathy and "wire loop" capillaries with or without fibrinoid necrosis of capillary loops, rupture of Bowman's capsule, and periglomerular inflammation and fibrosis ("crescent" formation) affecting less than 25% of the glomeruli. Focal synechiation of glomerular tuft to the Bowman's capsular epithelium is often present and may be the only prominent finding; if synechiation is the only finding, a score of 3 will be assigned if less than 75% of the glomerular tufts are affected.
4   Moderate to severe disease with same characteristics as score 3, but affecting 25-50% of the glomerular tufts
5   Severe disease with same characteristics as score 3, but affecting 50-75% of the glomerular tufts
6   Severe disease with same characteristics as score 3, but affecting greater than 75% of the glomerular tufts Scores 3-6 divide WHO scores III and IV into four sub-scores

TABLE 5B

Interstitial Inflammation

| | |
|---|---|
| 0 | No significant lesions |
| 1 | Minimal to mild inflammation and fibrosis |
| 2 | Mild to moderate inflammation and fibrosis |
| 3 | Moderate to severe inflammation and fibrosis |
| 4 | Severe and diffuse inflammation and fibrosis |

Scores 0-4, based on density of chronic inflammation (lymphocytes, plasma cells, and macrophages) with fibrosis within the interstitium and surrounding renal blood vessels Statistics—

Statistical analysis was conducted using Tukey's multiple comparison tests to determine whether significant differences existed between treatment groups. P values equal to or less than 0.05 were accepted as statistically significant.

Proteinuria and Albuminuria—

Figure 3:
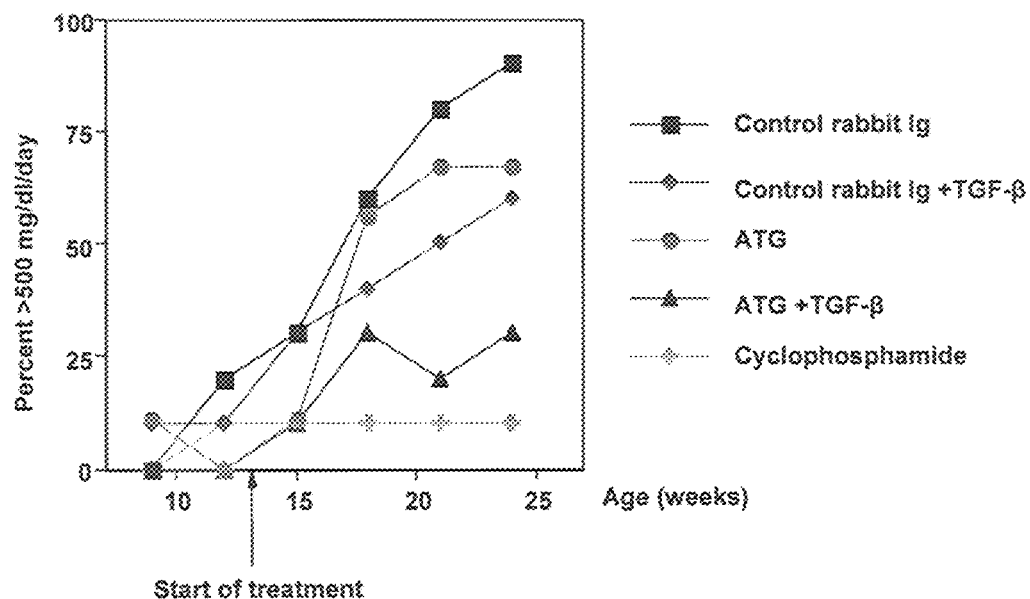
FIG. 3 shows the effect of the combination treatment on the development of severe kidney disease. Mice were treated as described above for FIG. 2. SLE mice treated with ATG and latent TGF-β1 together exhibited a decrease in the incidence of severe proteinuria (>500 mg/dl/day) as compared to SLE mice treated with either ATG alone, control Ig+TGF-β1, or control Ig alone.

Treatment with ATG or latent TGF-β1 alone (control Ig+TGFβ1) largely failed to inhibit the development of proteinuria (FIG. 2), although by the end of the study the incidence of severe proteinuria (>500 mg/dl/day) was slightly reduced in these single agent treatment groups compared to the mice treated with control Ig (60-67% vs. 90%, respectively) (FIG. 3). In contrast, treatment with a combination of ATG and latent TGF-β1 resulted in marked inhibition in the incidence (30% vs. 90%) and severity of proteinuria, suggesting a synergistic effect between these two agents (FIGS. 2 and 3).

Figure 4:
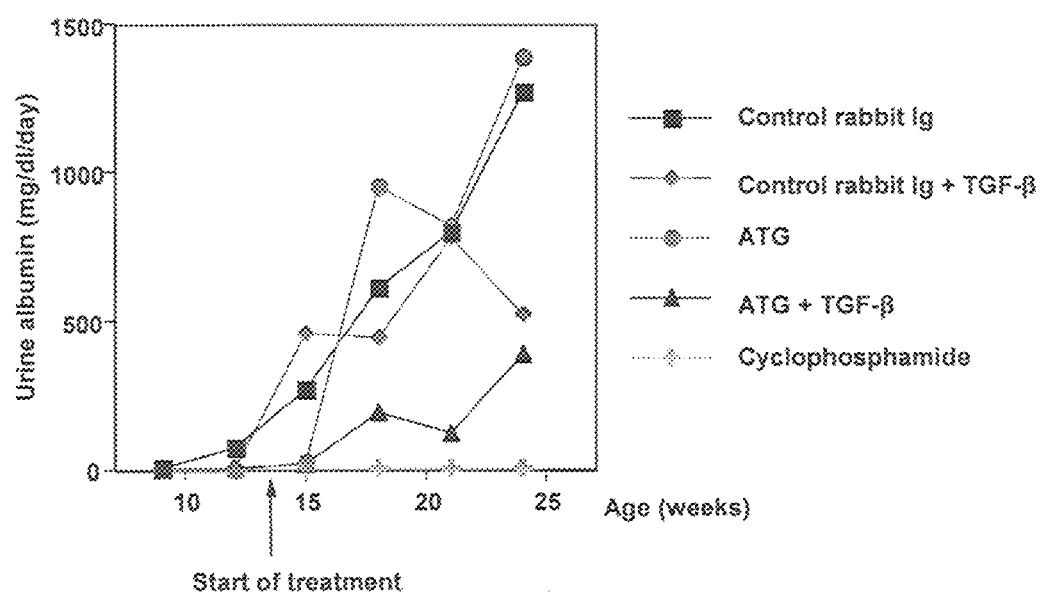
FIG. 4 shows the effect of the combination treatment on kidney function. Mice were treated as described above for FIG. 2. The mean urine albumin levels were decreased in SLE mice treated with the combination of ATG and latent TGF-β1 in comparison with SLE mice treated with either ATG alone, control Ig+TGF-β1, or control Ig alone. ATG and latent TGF-β1 combination treatment resulted in mean urine albumin levels near those achieved with cyclophosphamide treatment.
Figure 5:
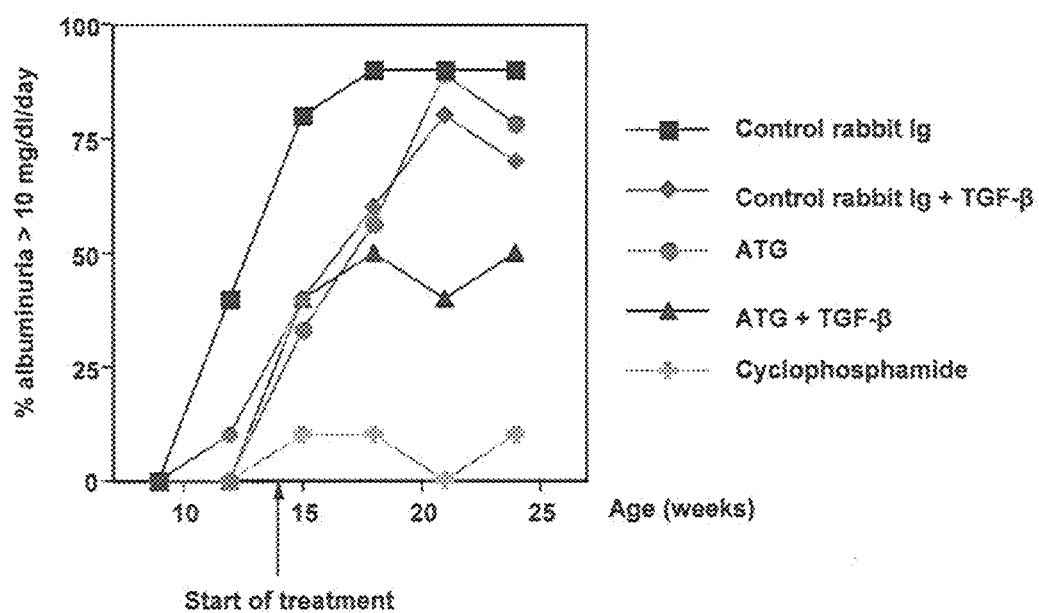
FIG. 5 shows the effect of the combination treatment on the development of severe kidney disease. Mice were treated as described above for FIG. 2. The percent of SLE mice having severe albuminuria (>10 mg/dl/day) was decreased in the combination treatment group in comparison with either ATG alone, control Ig+TGF-β1, or control Ig alone.

The observed reduction in the levels of total protein in the urine of mice treated with the combination of ATG and latent TGF-β1 was also reflected in the measurements of urine albumin levels (FIGS. 4 and 5). ELISA quantitation indicated that the incidence and severity of albuminuria was considerably reduced in mice treated with the combined therapy as compared either the negative control Ig group or the single agent therapy groups (ATG, control Ig+TGFβ1).

Antibodies to dsDNA—

Figures 6A, 6B:
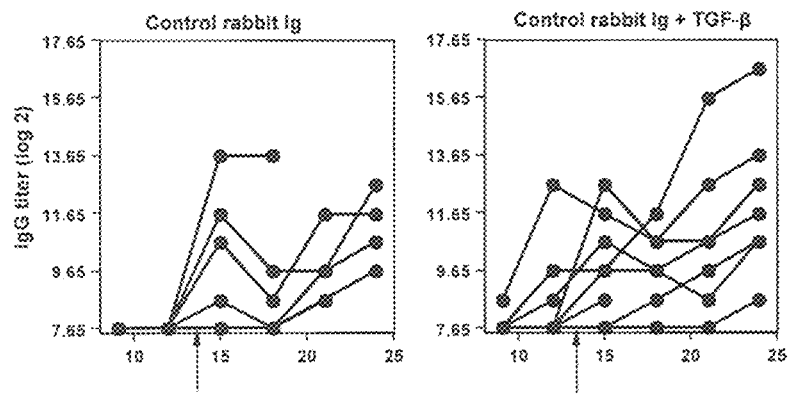
FIGS. 6A-6E show the effect of the combination treatment on the development of autoantibodies. Arrows indicate start of treatment. Mice were treated as described above for FIG. 2 and indicated accordingly in FIGS. 6A-6E. Overall, SLE mice treated with ATG and latent TGF-β1 showed a considerable delay in the rise of IgG anti-dsDNA antibody titers in comparison to mice treated with either ATG alone, control Ig+TGF-β1, or control Ig alone.
Figures 6C, 6D:
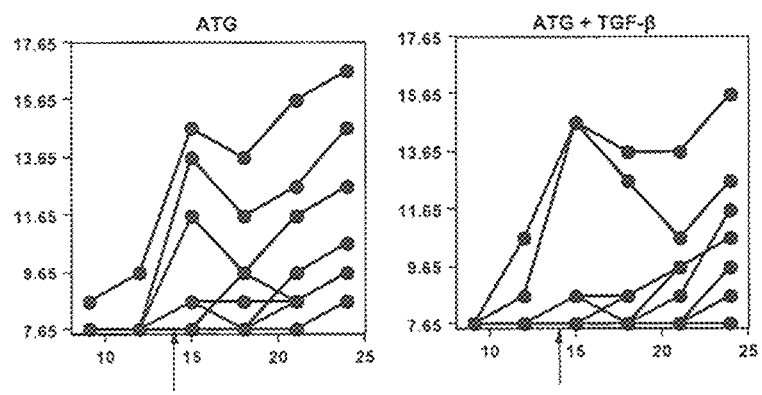
Figure 6E:
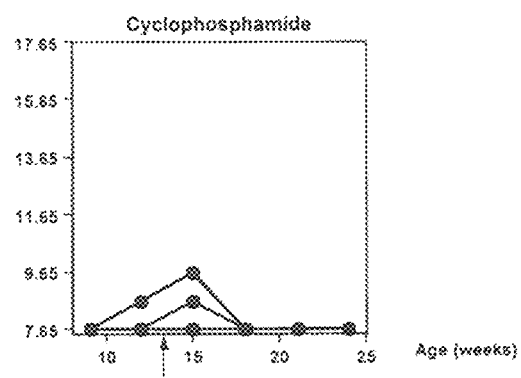

The majority of mice in the negative control group (normal rabbit Ig) as well as the latent TGF-β1+control Ig and ATG-treated groups, gradually developed rising titers of IgG antibodies against dsDNA with comparable kinetics. By comparison, there was a considerable delay in the rise of anti-dsDNA titers in the group treated with the combination of ATG and latent TGF-β1 (FIG. 6). Deposition of the immune complexes (DNA-anti-DNA complexes) in the glomeruli is believed to play an important role in the inflammation and renal pathology characteristic of lupus. However, the apparent inhibition in the development of antibodies to dsDNA in the combination treatment group could not entirely account for the preservation of kidney function, as there was a poor correlation between titers of antibodies and degree of proteinuria at the end of the study.

Survival—

Figure 7:
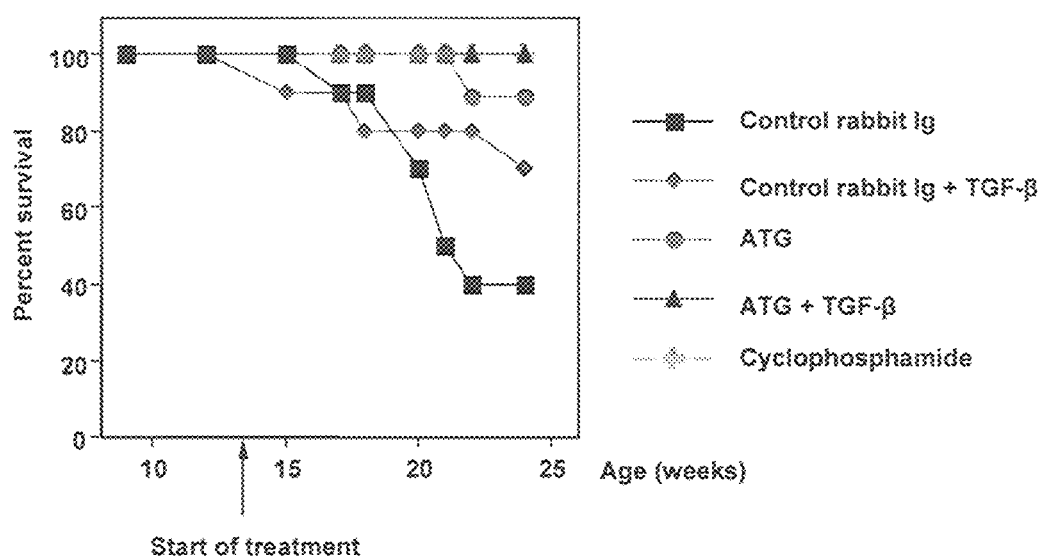
FIG. 7 shows the effect of the combination treatment on survival of SLE mice. Mice were treated as described above for FIG. 2. SLE mice treated with ATG and latent TGF-β1 survived significantly longer than SLE mice treated with either ATG alone, control Ig+TGF-β1, or control Ig alone.

Dosing with ATG and/or latent TGF-β1 was well tolerated and did not give rise to any obvious adverse events. All of the deaths, except for one animal in the latent TGF-β1+ control Ig group, were associated with very high levels of proteinuria and presumably resulted from kidney failure. All of the treatment groups showed an overall improvement in survival when compared to the negative control rabbit Ig-treated group (FIG. 7). The highest degree of survival (100%) was seen in the cyclophosphamide and the ATG/latent TGF-β1 combination treatment groups, followed by the ATG (90%) and latent TGF-β1+control Ig (70%) treatment groups. The negative control Ig group had only a 40% survival rate by the end of the study.

Histology—

The results of the histological analyses are presented in Table 6. Mice treated with ATG and latent TGF-β1 exhibited lesser degrees of glomerulopathy compared to control mice or mice that received either ATG alone or latent TGF-β1 and control Ig. These histologic findings correlated with clinical findings of decreased proteinuria/albuminuria and improved survival in the combination-treated animals.

A minimal decrease in inflammation scores was noted in groups treated with ATG, latent TGF-β1+control Ig and the combination of ATG and latent TGF-β1 in comparison to the group treated with control rabbit IgG alone.

TABLE 6

| Treatment Group | Glomeruli Score | Inflammation Score |
|---|---|---|
| Control Rabbit IgG | 4.3 ± 1.4 | 2.8 ± 0.4 |
| Latent TGF-β1 | 3.1 ± 0.8 | 2.6 ± 0.5 |
| ATG | 2.7 ± 0.5 | 2.4 ± 0.5 |
| ATG + Latent TGF-β1 | 2.3 ± 0.7 | 2.7 ± 0.5 |
| Cyclophosphamide | 1.0 ± 0.7 | 1.3 ± 0.5 |

Figure 8:
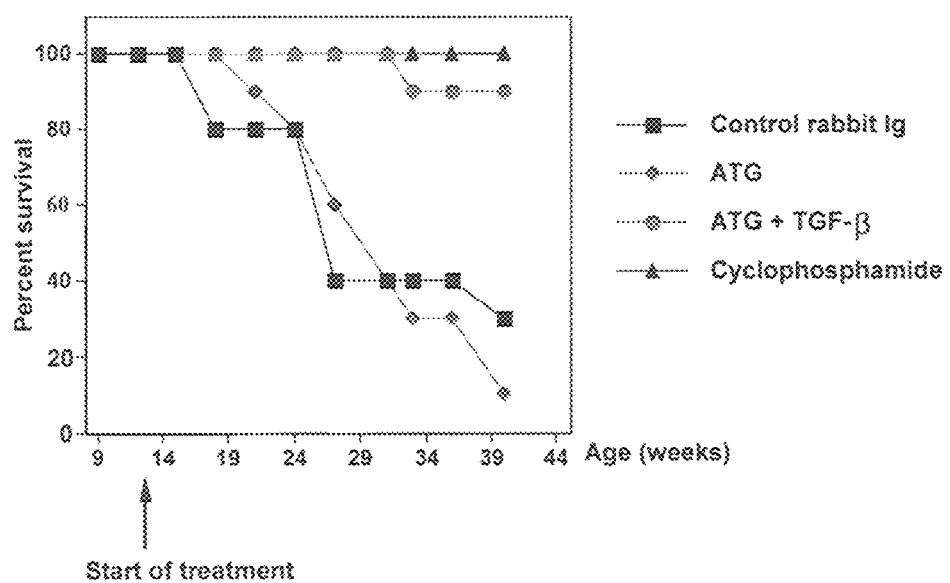
FIG. 8 shows the survival data obtained in a repeat study with MRL/MPJ-Tnfrs6$^{lpr}$ mice treated as described above for FIG. 2. In this instance, the study was extended to 40 weeks of age (as opposed to 24 weeks in the first study) to assess the durability of the effect of transient treatment with ATG and latent TGF-β1. The survival benefit did in fact persist and the survival of mice treated with ATG and latent TGF-β1 was comparable to that obtained with cyclophosphamide, the positive control (90% vs. 100%, respectively).

A repeat study was performed with MRL/MPJ-Tnfrs6$^{lpr}$ mice following the same treatment regimen as described above. In this instance, the study was extended to 40 weeks of age (as opposed to 24 weeks in the first study) to assess the durability of the effect of transient treatment with ATG+ latent TGF-β1. The results showed a long-term survival benefit. A 90% survival rate was observed in mice treated with ATG and latent TGF-β1 as compared to 30% survival in mice receiving control rabbit Ig, and 10% survival in the group treated with ATG. This compares favorably with cyclophosphamide which provided 100% survival but required chronic weekly injections as opposed to a one time transient course of treatment with ATG+latent TGF-β1 (FIG. 8).

A similar study was conducted in NZB/NZWF1 mice, another model of spontaneous lupus. The same treatment regimen was used and, under these conditions, there was no statistically significant effect of treatment with ATG and latent TGF-β1 or either agent alone, on the course or severity of disease. Due to differences in the characteristics and kinetics of disease between the two models, it is likely that the treatment regimen needs to be optimized for the NZB/NZWF1 strain.

To investigate the mechanism of action underlying the activity of ATG+TGF-β1, spleen cells from MRL/lpr lupus mice were cultured in vitro with ATG+/−TGF-β1 and the cells recovered were analyzed by FACS for the presence of Tregs. Pooled spleen cells from ten MRL/lpr mice with active disease (~25 weeks old) were resuspended at $2 \times 10^6$ cells/ml in serum-free AIM-V medium (Gibco, Grand Island, N.Y.) supplemented with 100 U/ml penicillin, 100 μg/ml streptomycin and 2 mM glutamine. The cells were cultured in 24-well plates containing 2 ml cells/well under six different conditions (8 wells/condition): 1) cells alone, 2) ATG (100 μg/ml)+active TGF-β1 (10 ng/ml; Genzyme), 3) ATG alone (100 μg/ml), 4) control rabbit IgG (100 μg/ml)+ active TGF-β1 (10 ng/ml), 5) control rabbit IgG alone (100 μg/ml), and 6) active TGF-β1 alone (10 ng/ml). Active TGF-β1 was used to mimic the activation process that would normally occur in vivo. The cells were incubated for five days at 37° C. and 5% $CO_2$. Cells from each culture condition were then pooled, washed in phosphate buffered saline, counted, and stained for FACS analysis. A total of $5 \times 10^5$ cells per sample were stained with rat anti-mouse CD4-Alexa 488 (Cat. No. 557667; BD Pharmingen, San Diego, Calif.) and rat anti-mouse CD25-PerCp-Cy5.5 (Cat No. 551071; BD Pharmingen). For intracellular detection of FOXP3, cells stained for surface CD4/CD25 were permeabilized overnight and stained using the eBioscience (San Diego, Calif.) FOXP3 staining kit (Cat. No. 72-5775) according to manufacturer's instructions. An acquisition of 6,000 lymphocytes per treatment was analyzed for staining on a FACS Calibur system (Becton Dickinson, San Diego, Calif.). Results are expressed as the absolute number of cells of each phenotype recovered under each culture condition (percent positive cells by FACS×total number of cells recovered from the culture).

Figure 9A:
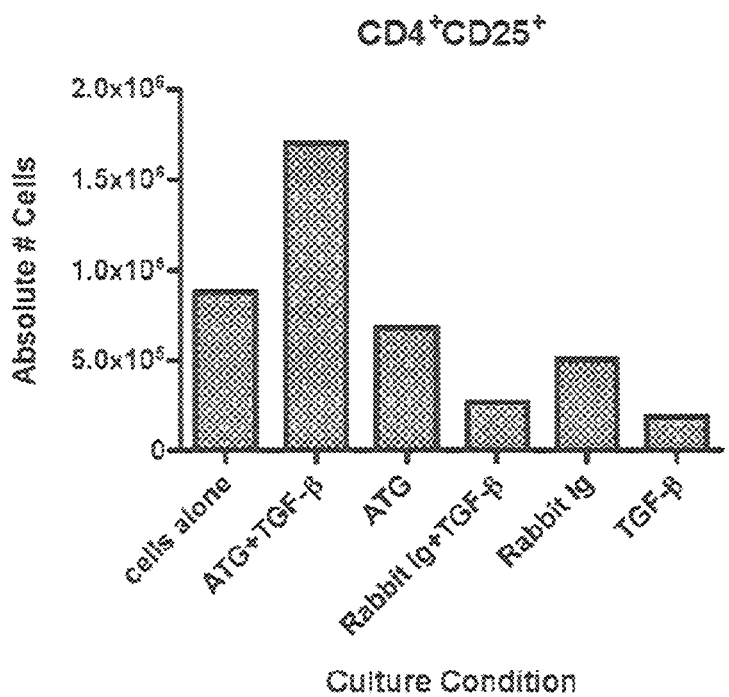
FIG. 9A shows the absolute number of CD4$^+$ CD25$^+$ cells in cultures of splenocytes exposed to various treatments. Splenocytes were pooled from ten MRL/lpr mice with active disease. Six different conditions (8 wells/condition) were assayed: 1) cells alone, 2) ATG (100 μg/ml)+active TGF-β1 (10 ng/ml; Genzyme), 3) ATG alone (100 μg/ml), 4) control rabbit IgG (100 μg/ml)+active TGF-β1 (10 ng/ml), 5) control rabbit IgG alone (100 μg/ml), and 6) active TGF-β1 alone (10 ng/ml). After five days, the replicates of each culture condition were pooled, washed in phosphate buffered saline, counted, and stained for FACS analysis. A sample of 5×10$^5$ cells per treatment was stained with rat anti-mouse CD4-Alexa 488 and rat anti-mouse CD25-PerCp-Cy5.5 and analyzed by flow cytometry. An acquisition of 6,000 lymphocytes per treatment was analyzed for staining on a FACS Calibur system (Becton Dickinson, San Diego, Calif.). Results are expressed as the absolute number of cells of each phenotype recovered under each culture condition (percent positive cells by FACS×total number of cells recovered from the culture).
Figure 9B:
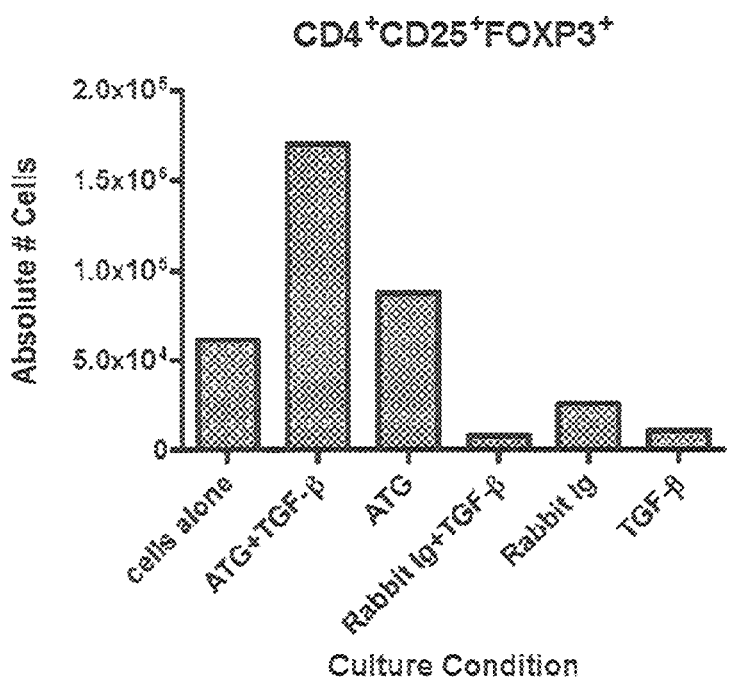
FIG. 9B shows the absolute number of CD4$^+$ CD25$^+$ FOXP3$^+$ cells in cultures of splenocytes treated as described for FIG. 9A. Additionally, for intracellular detection of FOXP3, cells stained for surface CD4/CD25 were permeabilized overnight and stained for FOXP3.

As shown in FIG. 9, the number of $CD4^+CD25^+$ T cells recovered was the greatest in cultures containing ATG+TGF-β1. Regulatory T cells typically express a $CD4^+CD25^+$ phenotype but activated T cells can also exhibit this phenotype. Additional FOXP3 staining provides further evidence of a Treg phenotype and the results obtained confirmed that treatment with ATG+TGF-β1 produced the greatest number of $CD4^+CD25^+FOXP3^+$ Tregs. Treatment with ATG alone also appeared to lead to a slight increase in this population (compared to cells alone) which was enhanced by the addition of TGF-β1. These results support the hypothesis that treatment with ATG+TGF-β1 can promote the expansion of Tregs and that such cells may provide a therapeutic benefit under conditions of autoimmunity.

Murine Model of Arthritis

The effect of ATG+/−TGF-β1 was tested in a collagen-induced arthritis mouse model. To induce disease, DBA/1 mice (Jackson Laboratory) were immunized on day 0 with bovine type II collagen (Cat. No. 2002-2, Chondrex) in complete Freund's adjuvant in a 100 μl total volume at the base of the tail. A booster immunization with collagen in incomplete Freund's adjuvant was given on day 22. Treatment with ATG or control rabbit IgG consisted of two intraperitoneal (i.p.) injections of 500 μg (~25 mg/kg) delivered three days apart (days 23 and 26). Latent TGF-β1 was given from days 28-37 as ten daily i.p. injections of 4 μg per mouse. A 4 μg dose of latent TGF-β1 corresponds to a 1 μg (~0.05 mg/kg) dose of the active (mature, non-LAP-associated) portion of the molecule. The treatment groups included (1) control rabbit IgG, (2) control rabbit IgG+latent TGF-β1, (3) ATG, and (4) ATG+latent TGF-β1, with ten animals per group. Starting on day 21, individual mice were examined and scored for clinical signs of disease 2-3 times per week. The arthritic score scale is defined in Table 7.

TABLE 7

| Severity Score | Gross Pathology |
|---|---|
| 0 | No evidence of erythema and swelling |
| 1 | Erythema and mild swelling confined to the mid-foot (tarsals) or ankle joint |
| 2 | Erythema and mild swelling extending from the ankle to the mid foot |
| 3 | Erythema and moderate swelling extending from the ankle to the metatarsal joints |
| 4 | Erythema and severe swelling encompass the ankle, foot, and digits |

Each paw is assessed individually and the arthritic score for a given mouse is the sum of the scores for all paws (maximum score of 16)

Treatment with ATG alone resulted in a reduction in disease scores and the addition of latent TGF-β1 did not appear to provide an additional benefit under the conditions tested. The results are shown in Table 8.

TABLE 8

| | Arthritic Score (Mean ± SEM) | | | |
|---|---|---|---|---|
| Day | Rabbit Ig | Rabbit Ig + Latent TGF-β1 | ATG | ATG + Latent TGF-β1 |
| 22 | 0.0 ± 0.0 | 0.0 ± 0.0 | 0.0 ± 0.0 | 0.0 ± 0.0 |
| 26 | 2.7 ± 2.3 | 3.7 ± 2.5 | 2.8 ± 2.6 | 5.0 ± 3.5 |
| 29 | 10.0 ± 4.2 | 10.1 ± 4.3 | 3.4 ± 4.9 | 5.8 ± 5.3 |
| 32 | 10.5 ± 4.4 | 11.6 ± 3.0 | 5.5 ± 6.0 | 6.6 ± 5.1 |
| 35 | 10.5 ± 4.4 | 12.0 ± 2.7 | 6.5 ± 5.9 | 7.6 ± 4.3 |
| 39 | 10.9 ± 3.9 | 12.9 ± 2.0 | 7.0 ± 5.5 | 8.1 ± 3.3 |
| 41 | 11.0 ± 4.1 | 12.5 ± 2.8 | 7.3 ± 5.2 | 8.8 ± 3.6 |
| 43 | 11.7 ± 3.7 | 13.4 ± 1.8 | 7.5 ± 5.4 | 8.9 ± 3.8 |
| 46 | 11.5 ± 4.5 | 13.4 ± 2.8 | 9.5 ± 5.1 | 9.1 ± 3.5 |
| 50 | 12.7 ± 3.0 | 13.5 ± 2.1 | 9.5 ± 4.9 | 9.0 ± 3.7 |
| 53 | 12.4 ± 4.0 | 13.8 ± 2.1 | 9.6 ± 4.8 | 9.3 ± 3.7 |
| 57 | 12.4 ± 4.0 | 13.8 ± 2.1 | 9.6 ± 4.8 | 9.3 ± 3.7 |

The collagen-induced arthritis is a short-term animal model, in which the treatment takes place on a timescale of weeks, versus months for the lupus model. This shorter timescale might be insufficient to observe the benefit added by administering TGF-β1 with the ATG, which was seen in the lupus model. Thus, different dosing regimens or further testing of additional animal models may show benefits of combined administration of ATG and latent TGF-β.

Murine Model of Uveitis

The effect of ATG+/−TGF-β1 was tested in a mouse model of uveitis. To induce disease, B10.RIII mice (Jackson Laboratory) were immunized subcutaneously on day 0 with 100 μg of amino acids 161-180 of human interphotoreceptor retinoid binding protein ($IRBP_{161-180}$) (custom synthesis, New England Peptide) in complete Freund's adjuvant at two sites (between shoulder blades and in pelvic region). Starting on day 10, funduscopic examinations were performed on individual mice and a disease score was assigned. To perform the examination, the eyes of mice were dilated using one or two drops of Mydriacyl™ 1% (Cat. No. 1120, JA Webster) and rested in a darkened room for approximately five minutes. Mice were manually restrained and the retinas of both eyes visualized using an indirect ophthalmoscope with a 78 diopter lens. The eyes were scored for inflammation using a progressive scoring system between 0 and 5, as described in Table 9.

TABLE 9

| Score | Gross Pathology |
|---|---|
| 0 | Normal retina |
| 1 | Vascular inflammation proximal to the optic nerve |
| 2 | >10 inflammatory lesions confined to one quadrant of the eye |
| 3 | >10 inflammatory lesions in more than one quadrant of the eye |
| 4 | Inflammatory lesions are contiguous |
| 5 | Retinal detachment |

Treatment with ATG or control rabbit IgG was initiated at disease onset (score of 1) and consisted of two i.p. injections of 500 µg (~25 mg/kg) delivered four days apart (days 10 and 14). Latent TGF-β1 was given from days 15-27 as thirteen daily i.p. injections of 4 µg per mouse. A 4 µg dose of latent TGF-β1 corresponds to a 1 µg (~0.05 mg/kg) dose of the active (mature, non-LAP-associated) portion of the molecule. The treatment groups included (1) phosphate buffered saline (PBS) control (2) control rabbit IgG, (3) control rabbit IgG+latent TGF-β1, (4) ATG, and (5) ATG+latent TGF-β1, with six animals per group. Treatment with ATG alone resulted in a reduction in disease scores and the addition of latent TGF-β1 did not appear to provide an additional benefit under the conditions tested. The results are shown in Table 10.

TABLE 10

| | Uveitis Score (Mean ± SEM) | | | | |
|---|---|---|---|---|---|
| Day | PBS | Rabbit Ig | Rabbit Ig + Latent TGF-β1 | ATG | ATG + Latent TGF-β1 |
| 8 | 0.00 ± 0.00 | 0.00 ± 0.00 | 0.00 ± 0.00 | 0.00 ± 0.00 | 0.00 ± 0.00 |
| 10 | 1.25 ± 0.16 | 1.22 ± 0.15 | 1.29 ± 0.18 | 1.13 ± 0.13 | 1.13 ± 0.23 |
| 14 | 4.00 ± 0.00 | 3.17 ± 0.32 | 3.67 ± 0.22 | 2.10 ± 0.48 | 2.17 ± 0.34 |
| 17 | 3.81 ± 0.10 | 3.00 ± 0.35 | 3.58 ± 0.29 | 1.75 ± 0.37 | 2.00 ± 0.37 |
| 21 | 3.81 ± 0.10 | 2.58 ± 0.34 | 3.33 ± 0.33 | 1.92 ± 0.42 | 2.08 ± 0.31 |
| 24 | 3.94 ± 0.06 | 2.58 ± 0.42 | 3.50 ± 0.34 | 2.00 ± 0.41 | 1.92 ± 0.36 |
| 29 | 3.75 ± 0.11 | 2.27 ± 0.47 | 3.33 ± 0.33 | 2.08 ± 0.42 | 2.00 ± 0.40 |
| 35 | 3.88 ± 0.09 | 2.25 ± 0.46 | 3.33 ± 0.40 | 1.92 ± 0.40 | 2.00 ± 0.35 |
| 46 | 3.56 ± 0.13 | 2.09 ± 0.41 | 3.25 ± 0.39 | 2.00 ± 0.44 | 1.92 ± 0.40 |
| 56 | 3.69 ± 0.12 | 2.17 ± 0.44 | 3.25 ± 0.39 | 1.67 ± 0.38 | 1.75 ± 0.25 |

The uveitis model is a short-term animal model, in which the treatment takes place on a timescale of weeks, versus months for the lupus model. This shorter timescale might be insufficient to observe the benefit added by administering TGF-β1 with the ATG, which was seen in the lupus model. Thus, different dosing regimens or further testing of additional animal models may show benefits of combined administration of ATG and latent TGF-β.

All publications, patents, patent applications, and biological sequences cited in this disclosure are incorporated by reference in their entirety.

The invention claimed is:

1. A method of treating a mammal with systemic lupus erythematosus, the method comprising:
   (a) depleting circulating lymphocytes in the mammal by administering to the mammal a therapeutically effective amount of an anti-thymocyte antibody,
   (b) allowing the lymphocytes to begin repopulating, and
   (c) during the repopulation phase of (b), administering to the mammal a therapeutically effective amount of latent TGF-β.

2. The method of claim 1, wherein the mammal is a human.

3. The method of claim 1, wherein the lymphocytes depleted are predominantly T cells.

4. The method of claim 1, wherein the anti-thymocyte antibody is chosen from the group consisting of rabbit anti-thymocyte globulin and equine anti-thymocyte globulin.

5. The method of claim 1, wherein latent TGF-β promotes the expansion of $CD4^+$ $CD25^+$ regulatory T cells.

6. The method of claim 1, wherein latent TGF-β comprises mature TGF-β and one or both of the following:
   (a) latency associated peptide (LAP); and
   (b) latent TGF-β binding protein (LTBP).

7. The method of claim 1, wherein latent TGF-β is TGF-β1.

8. The method of claim 1, wherein latent TGF-β is administered systemically.

9. The method of claim 1, wherein step (c) further comprises administering rapamycin to the mammal.

10. The method of claim 1, wherein the systemic lupus erythematosus is associated with a loss of kidney function and the treatment results in slowing of the loss of or improvement in kidney function of the mammal.

11. The method of claim 10, wherein the slowing of loss or improvement in kidney function is indicated by a change in systemic blood pressure, proteinuria, albuminuria, glomerular filtration rate, and/or renal blood flow.

12. The method of claim 1, wherein step (c) further comprises administering to the mammal one or more agents chosen from the group consisting of:
   (a) vitamin D3,
   (b) dexamethasone, and
   (c) mycophenolate mofetil.

13. A method of treating a mammal with systemic lupus erythematosus, comprising:
   (a) administering an anti-thymocyte antibody to the mammal, thereby reducing the population of peripheral blood T cells; and
   (b) administering latent TGF-β to the mammal in an amount effective to slow the progression of systemic lupus erythematosus and/or improve symptoms.

* * * * *